United States Patent [19]

Finch

[11] Patent Number: 5,507,780
[45] Date of Patent: Apr. 16, 1996

[54] SELECTIVE DEFAULT DATA STORAGE FOR AN IMPLANTABLE ATRIAL DEFIBRILLATOR

[76] Inventor: David P. Finch, 15008 - 91st Pl. NE., Bothell, Wash. 98011

[21] Appl. No.: 377,913

[22] Filed: Jan. 25, 1995

[51] Int. Cl.⁶ .............................. A61N 1/00; A61N 1/39
[52] U.S. Cl. .................. 607/5; 607/4; 607/6; 128/705; 128/734
[58] Field of Search .................. 607/5, 9, 7, 10, 607/36, 4, 14; 128/695, 696, 700, 705, 697

[56] References Cited

U.S. PATENT DOCUMENTS

| | | | |
|---|---|---|---|
| 3,862,636 | 1/1975 | Bell et al. | 607/5 |
| 4,830,006 | 5/1989 | Haluska et al. | 607/5 |
| 5,048,521 | 9/1991 | Pless et al. | 607/5 |
| 5,179,945 | 1/1993 | Van Hofwegen et al | 607/5 |
| 5,366,486 | 11/1994 | Zipes et al. | 607/5 |

*Primary Examiner*—Angela D. Sykes
*Assistant Examiner*—Stephen Huang
*Attorney, Agent, or Firm*—Richard O. Gray, Jr.

[57] ABSTRACT

A defibrillator, such as an atrial defibrillator, applies cardioverting electrical energy to the atria of a heart when the atria are in need of cardioversion. The atrial defibrillator includes an atrial sense channel for sensing atrial activity and ventricular sense channels for sensing ventricular activity to generate heart activity data, a memory for storing the heart activity data, and a cardiovertor which applies cardioverting electrical energy to the atria if the heart activity satisfies a predetermined criteria. A storage control causes at least a portion of the heart activity data to be retained in the memory if the heart activity data fails to satisfy the predetermined criteria.

20 Claims, 2 Drawing Sheets

SELECTIVE DEFAULT DATA STORAGE FOR AN IMPLANTABLE ATRIAL DEFIBRILLATOR

BACKGROUND OF THE INVENTION

The present invention generally relates to an atrial defibrillator which applies cardioverting electrical energy to the atria of a human heart when activity of the heart satisfies predetermined criteria. The present invention more particularly relates to such an atrial defibrillator which further selectively stores heart activity data related to the failure of the heart activity to satisfy the predetermined criteria after detection of an atrial fibrillation episode. The selectively stored data, herein referred to as "default data", includes data relating to the failure to confirm the initial detection of atrial fibrillation, failure to identify required heart activity conditions to enable an attempted cardioversion of the atria, or an inability to redirect atrial fibrillation or confirm reelection of atrial fibrillation after an attempted cardioversion of the atria.

Atrial fibrillation is probably the most common cardiac arrhythmia. Although it is not usually a life threatening arrhythmia, it is associated with strokes. Such strokes are thought to be caused by blood clots formed in areas of stagnant blood flow resulting from prolonged episodes of atrial fibrillation. In addition, patients afflicted with atrial fibrillation generally experience palpitations of the heart and may even experience dizziness or even loss of consciousness due to decreased cardiac output.

Atrial fibrillation occurs suddenly and many times can only be corrected by a discharge of electrical energy to the heart through the skin of the patient by way of an external defibrillator of the type well known in the art. This treatment is commonly referred to as synchronized cardioversion and, as its name implies, involves applying electrical defibrillating energy to the heart in synchronism with a detected ventricular electrical activation (R wave) of the heart. The treatment is very painful and, unfortunately, most often only results in temporary relief for patients, lasting but a few weeks.

Drugs are available for reducing the incidence of atrial fibrillation. However, these drugs have many side effects and many patients are resistant to them which greatly reduces their therapeutic effect.

Implantable atrial defibrillators have been proposed to provide relief to patients suffering from occurrences of atrial fibrillation. Unfortunately, to the detriment of such patients, none of these atrial defibrillators have become a commercial reality. Two such proposed defibrillators, although represented as being implantable, required human interaction for cardioverting or defibrillating the heart (along with requiring a patient to recognize the symptoms of atrial fibrillation). One such defibrillator required the patient to visit a physician to activate the defibrillator. The other defibrillator required the patient to activate the defibrillator from external to the patient's skin with a magnet.

An improved atrial defibrillator is fully disclosed in U.S. Pat. No. 5,282,837, entitled IMPROVED ATRIAL DEFIBRILLATOR AND METHOD, which issued on Feb. 1, 1994 in the names of John M. Adams and Clifton A. Alferness. This patent is assigned to the assignee of the present invention and is incorporated herein by reference.

The atrial defibrillator of the above-referenced patent provides automatic operation. It senses activity of the heart and firstly determines if the heart is in atrial fibrillation by examining the heart ventricular rate, the ventricular rate variability, and the atrial activity. The ventricular rate and variability are used to predict the probability of atrial fibrillation when the rate and variability exceed a limit. The atrial activity is examined to determine with greater certainty if atrial fibrillation is present. When all of the atrial fibrillation detection criteria are satisfied, the atrial defibrillator cardioverts the atria of the heart.

The atrial defibrillator of the above-referenced patent includes further features and advantages. For example, it provides R wave detection of increased reliability for synchronizing the delivery of the cardioverting electrical energy to the atria with an R wave of the heart. This assists in avoiding the T wave vulnerable period of the heart when applying the cardioverting electrical energy to the heart. Further, as another feature, a lead system having electrodes in and near the heart reduces the amount of cardioverting electrical energy required to cardiovert the atria of the heart. This not only reduces energy consumption to prolong the useful life of the defibrillator, but, more importantly, reduces the potential discomfort to the patient during cardioversion.

Further improvements in implantable automatic atrial defibrillators are described in U.S. Pat. No. 5,207,219, which issued on May 4, 1993, for ATRIAL DEFIBRILLATOR AND METHOD FOR PROVIDING INTERVAL TIMING PRIOR TO CARDIOVERSION, and which is also assigned to the assignee of the present invention and incorporated herein by reference. The atrial defibrillator there disclosed provides an answer to the observation that during episodes of atrial fibrillation, the cardiac rate increases to a high rate and/or becomes extremely variable. At high or variable cardiac rates, the R wave of a cardiac cycle may become closely spaced from the T wave of the immediately preceding cardiac cycle. This creates a condition known in the art as an "R on T" condition which is believed to contribute to induced ventricular fibrillation if the atria are cardioverted in synchronism with the R wave close to the preceding T wave. In order to prevent cardioversion of the atria during an R on T condition, the atrial defibrillator described in U.S. Pat. No. 5,207,219 detects for a cardiac interval longer than a minimum interval prior to delivering the cardioverting electrical energy to the atria. This assures that the cardioverting electrical energy is not delivered during an R on T condition.

As can be seen from the foregoing, there is a complex criteria which the heart activity must satisfy for the automatic detection and cardioversion of atrial fibrillation. Such criteria may relate to both ventricular and atrial activity of the heart to detect fibrillation of the atria. The criteria may further relate to cardiac intervals immediately prior to cardioversion and the successful detection of R waves to assure that the application of the cardioverting electrical energy is synchronized with an R wave and avoids a T wave. The criteria may also relate to the quality of the cardiac signals or data derived therefrom as a prerequisite to evaluating the signals or data for detecting atrial fibrillation and applying cardioverting energy.

In addition to the foregoing, defibrillators have been developed which are capable of storing information relating to the successful detection and cardioversion of fibrillation. Generally, the stored information takes the form of digital samples representative of selected electrograms related to the detection of a fibrillation episode and the successful cardioversion of the detected fibrillation episode.

One such defibrillator is described in copending application Ser. No. 08/264,319, filed Jun. 23, 1994, in the names of Barry M. Yomtov and David P. Finch, for SELECTIVE DATA STORAGE FOR AN AUTOMATIC IMPLANTABLE ATRIAL DEFIBRILLATOR, which application is assigned to the assignee of the present invention and incorporated herein by reference. The defibrillator described in that application is an atrial defibrillator which stores, in memory, electrogram data related to the activity of the heart occurring during a discrete time period prior to detection of atrial fibrillation and electrogram data associated with the activity of the heart occurring during a second discrete time period commencing before cardioversion of the heart and extending continuously until after cardioversion of the heart. Once stored, this data may be transmitted through a telemetry link to an external receiver for display or chart recording to facilitate later confirmation of successful detection and cardioversion.

While such confirming data is of great importance to the cardiologist in monitoring patients, other information, not contemplated by the prior art to be stored, would also be of importance if made available. For example, data which may reveal the cause of a failure to treat a fibrillation episode once it is detected would also have utility. Such data would be especially helpful where a complex criteria must be satisfied to detect fibrillation, confirm such detection, and then apply cardioverting energy. Failure to treat a fibrillation episode could be caused by the failure to satisfy one or more different aspects of a complex criteria. Data relating to the failure to satisfy that criteria could facilitate corrective adjustment of programmable parameters of an implanted defibrillator to enable successful operation of such a device and the provision of appropriate therapy when required. It could also assist in revealing other operational problems, such as heart activity sensing difficulties resulting from sensing electrode migration or attempted operation in an environment having high electromagnetic interference.

SUMMARY OF THE INVENTION

The present invention therefore provides a defibrillator including sensing means for sensing electrical activity of a heart and generating heart activity data, and processing means for analyzing the heart activity data to determine if the data satisfies a predetermined criteria. The defibrillator further includes cardioverting means responsive to the processing means for applying cardioverting electrical energy to the heart when the data satisfies the predetermined criteria, and storage means responsive to the processing means for storing at least a portion of the data when the data fails to satisfy the predetermined criteria.

The present invention more particularly provides for an atrial defibrillator for applying cardioverting electrical energy to the atria of a heart when the atria are in need of cardioversion. The atrial defibrillator includes sensing means for sensing atrial activity of the heart and generating atrial activity data, memory means for storing atrial activity data generated by the sensing-means, and processing means including an atrial fibrillation detector for determining if the atrial activity data satisfies atrial fibrillation criteria. The atrial defibrillator further includes cardioverting means for applying cardioverting electrical energy to the atria if the atrial activity data satisfies the atrial fibrillation criteria, and storage control means for causing at least a portion of the atrial activity data to be retained in the memory means if the atrial activity data fails to satisfy the atrial fibrillation criteria.

The present invention further provides a method of defibrillating a heart. The method includes the steps of sensing electrical activity of the heart and generating heart activity data, analyzing the heart activity data to determine if the data satisfies a predetermined criteria, applying cardioverting electrical energy to the heart when the data satisfies the predetermined criteria, and storing at least a portion of the data in a memory when the data fails to satisfy the predetermined criteria.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawing, in the several figures of which like reference numerals identify identical elements, and wherein:

DETAILED DESCRIPTION OF THE PREFERRED EMBODIMENT

Figure 1:
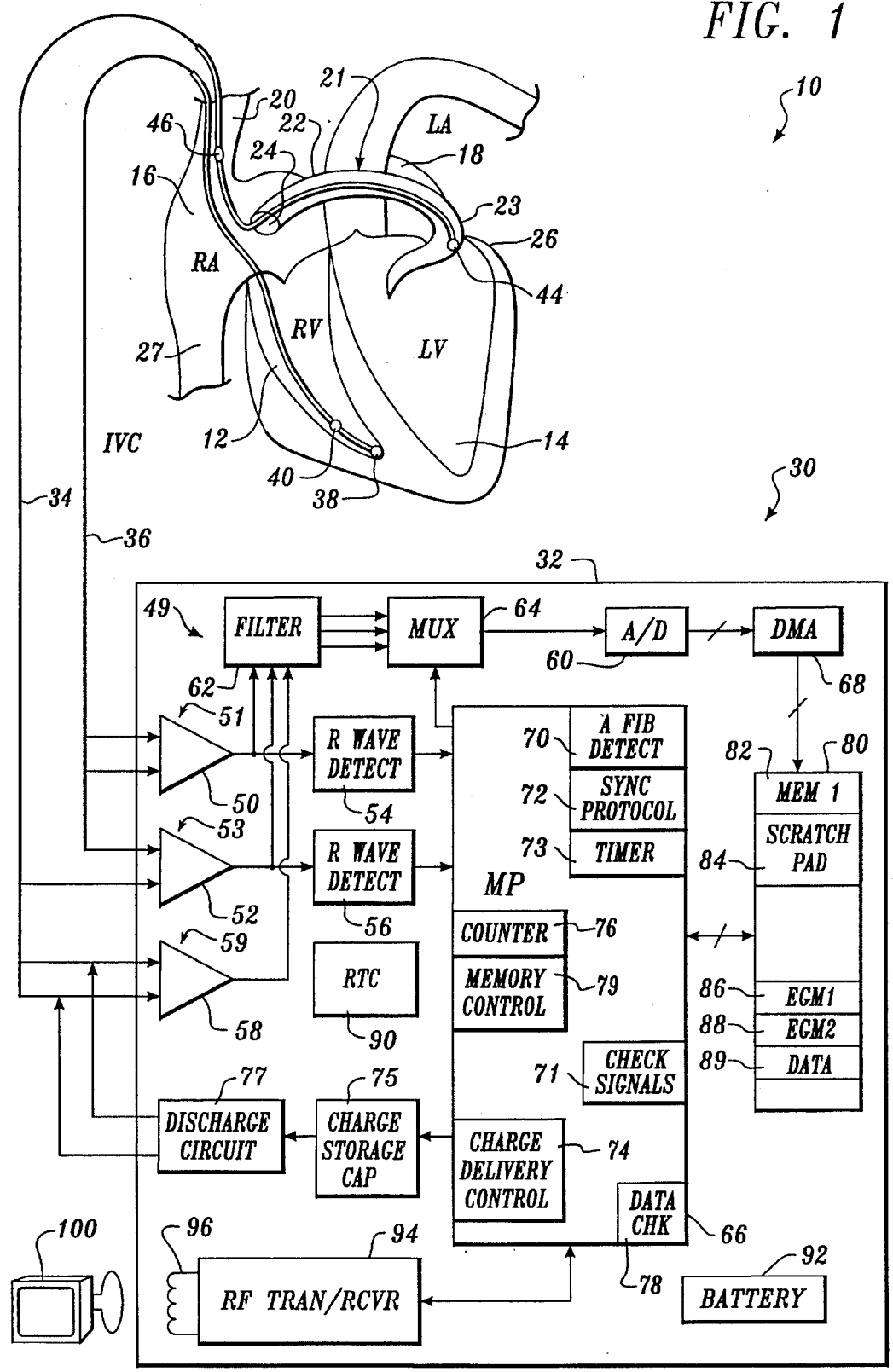
FIG. 1 is a schematic block diagram of a fully implantable atrial defibrillator embodying the present invention.

Referring now to FIG. 1, it illustrates an implantable automatic atrial defibrillator 30 embodying the present invention. The atrial defibrillator 30 includes an implantable enclosure 32 and an implantable lead system including an intravascular lead 34 and an endocardial lead 36. The endocardial lead 36 has tip and ring electrodes 38 and 40 respectively adapted for placement in the right ventricle 12. The intravascular lead 34 has a tip electrode 44 adapted for placement in the coronary sinus 22 or the great cardiac vein 23 and a ring electrode 46 adapted for placement in the superior vena cava 20 or right atrium 16. An alternative lead system may include separate leads for electrodes 44 and 46. This requires an additional endocardial lead (not shown in FIG. 1) adapted for placing electrode 46 in the superior vena cava 20 or the right atrium 16.

Electrodes 44 and 46 sense atrial activity of the heart and may be referred to herein as a first electrode pair. Electrodes 44 and 46 perform the additional function of applying cardioverting electrical energy across the atria 16 and 18 of the heart.

Electrodes 38 and 40 sense R waves of the heart and may be referred to herein as the second electrode pair. Electrode 44 together with either electrode 38 or electrode 40 also sense R waves of the heart and may be referred to herein as the third electrode pair. The dual sensing of the R waves between the second and third electrode pairs is performed for the purpose of reliably sensing R waves for synchronized cardioversion.

The implantable enclosure 32 includes a microprocessor 66 and a memory 80. The microprocessor controls the overall function of the atrial defibrillator 30 under software controlled by operating instructions and data stored in the memory 80. In addition to storing the operating instructions for the microprocessor 66, the memory 80 further stores electrogram samples as confirmation data for confirming successful atrial fibrillation detection and cardioversion, or as default data to permit analysis of the failure to attempt cardioversion after initial atrial fibrillation detection. To that end, the memory 80 includes a first memory portion 82, a scratch pad memory portion 84, a memory portion 86 (EGM1), a memory portion 88 (EGM2), and a default data memory portion 89.

Within the enclosure 32, the atrial defibrillator 30 further includes a sense amplifier 50 coupled to electrodes 38 and 40 of lead 36 to form an RV sense channel 51 and a sense amplifier 52 coupled to electrode 44 of lead 34 and to either electrode 38 or electrode 40 of lead 36 to form an RVCS sense channel 53. The sense amplifiers 50 and 52 amplify the electrogram signals provided by the second and third pairs of electrodes, respectively, and provide R wave detectors 54 and 56, respectively, with an amplified output. The R wave detectors 54 and 56 each include a threshold circuit which isolates the R waves from the amplified electrograms provided by sense amplifiers 50 and 52. The outputs of the R wave detectors 54 and 56 are coupled to the microprocessor for conveying the isolated R waves to the microprocessor 66.

Another sense amplifier 58 within enclosure 32 is coupled to electrodes 44 and 46 of lead 34 to form an atrial sense channel 59. The sense amplifier 58 provides an amplified output of the electrograms sensed by the first electrode pair consisting of electrodes 44 and 46. The electrograms provided by sense amplifier 58 predominantly represent atrial activity of the heart 10.

The output of each of the sense amplifiers 50, 52, and 58 is coupled to an analog-to-digital converter 60 through a filter 62 and a multiplexer 64. The analog-to-digital converter 60 digitizes the electrograms provided by the sense channels 51, 53 and 59 to generate electrogram digital data samples. The multiplexer 64 sequentially directs the electrogram signals from sense channels 51, 53 and 59 to the analog-to-digital converter 60. The electrogram samples are then conveyed to a direct memory access 68 which then stores the electrogram samples in the memory portion 82 of memory 80.

In controlling the function of the atrial defibrillator 30, the microprocessor 66 implements an atrial fibrillation detection algorithm represented by an atrial fibrillation detector 70. The microprocessor 66 further implements synchronization protocol 72 and charge delivery control 74. The microprocessor 66 still further, as will be discussed hereinafter, implements a timer 73, a counter 76, a check signals stage 71, a data check stage 78, and a memory control 79.

When the atrial fibrillation detector 70 determines that the activity of the heart 10 satisfies an atrial fibrillation criteria and hence is in atrial fibrillation, the microprocessor 66 under software control performs charge and delivery control operations pursuant to operating instructions obtained from the memory 80 to implement the charge and delivery control 74. The charge and delivery control 74 first causes the charger of circuit 75 to charge the storage capacitor therein to a selected peak voltage. The charge and delivery control 74 monitors the charging of the capacitor. When the charge delivery control 74 determines that the voltage across the storage capacitor has reached a selected peak voltage, the microprocessor, through the charge and delivery control 74, terminates the charging.

After the charging of the storage capacitor is completed, and after other criteria are satisfied, as will be described hereinafter, the microprocessor causes the discharge circuit 77, which is coupled to the storage capacitor of circuit 75, to discharge a portion of the stored energy. The discharged energy is applied to electrodes 44 and 46 of the intravascular lead 34 for applying the cardioverting electrical energy to the atria 16 and 18 of the heart 10.

After the cardioverting energy is applied to the atria, the atrial defibrillator 30 again applies its atrial fibrillation criteria to the heart activity to determine if the cardioversion was successful in arresting the atrial fibrillation episode. If the cardioversion was not successful, the cardioversion sequence is repeated at the same or a next higher energy level.

The entire cardioversion sequence from original detection of an atrial fibrillation episode through successful cardioversion is initiated at periodic intervals under the control of a real time clock 90. The periodic interval is a programmable parameter of the atrial defibrillator 30 and provides periodic wakeup for the detection and cardioversion of atrial fibrillation. Atrial fibrillation is not a life-threatening malady. Hence, unlike ventricular defibrillators which must continuously detect for ventricular fibrillation, the atrial defibrillator 30 detects for atrial fibrillation at periodic intervals in order to conserve power provided by a battery 92.

Lastly, the atrial defibrillator 30 includes an RF transmitter/receiver 94 within enclosure 32. The RF transmitter/receiver includes a coiled antenna 96 for communicating through telemetry to an external programmer 100. The telemetry link provided by the RF transmitter/receiver 94 and the external programmer 100 permits the cardiologist to program the atrial defibrillator 30 with respect to its various programmable parameters and to enable the cardiologist to read from the atrial defibrillator 30 certain data which has been stored in the memory 80, including selectively stored confirmation or default electrogram data.

The external programmer 100 includes a receiver for receiving transmitted data from the atrial defibrillator 30, including the electrogram digital samples stored in the memory portions 86, 88 and 89. The external programmer 100 preferably initiates all transmissions from the atrial defibrillator. It further includes memory and a display. After the electrogram digital samples are received by the external programmer and stored in memory, the electrograms may then be displayed on the display.

Figure 2:
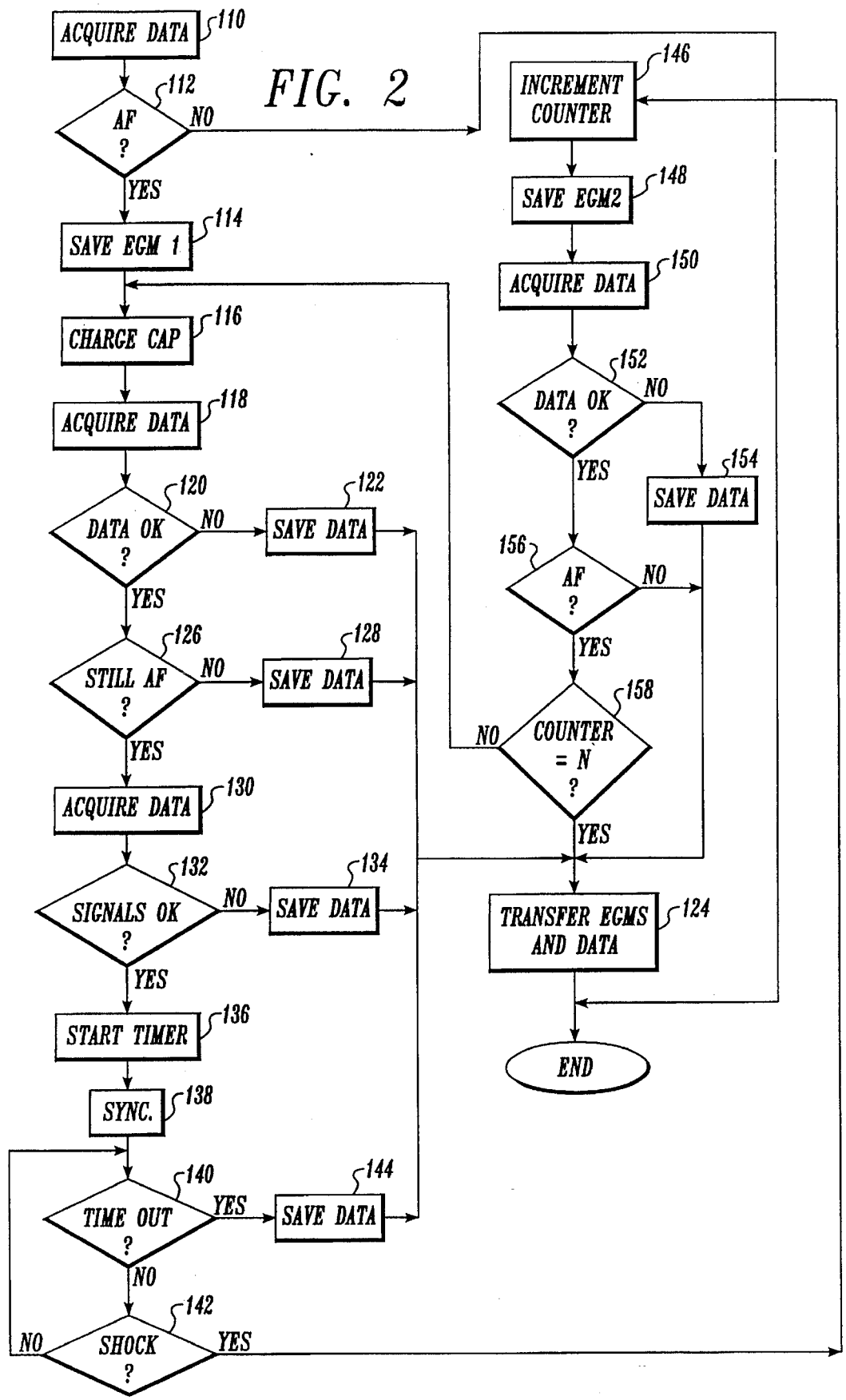
FIG. 2 is a flow diagram illustrating the manner in which the atrial defibrillator of FIG. 1 may be implemented for storing selected default data related to the inability to successfully cardiovert a detected atrial fibrillation episode in accordance with a preferred embodiment of the present invention.

Now that the atrial defibrillator 30 and its operation has been generally described, the defibrillator 30 and the manner in which it applies a predetermined criteria to detect an atrial fibrillation episode, to cardiovert the atrial fibrillation episode, and to achieve various data storage of electrogram samples, including default data in accordance with the present invention, will now be described with greater detail and with reference to the preferred embodiment as shown in the flow diagram of FIG. 2. As previously mentioned, the real time clock 90 causes the atrial defibrillator 30 to initiate detection of an atrial fibrillation episode at periodic intervals. When the atrial defibrillator 30 is to detect for an atrial fibrillation episode, the real time clock first initiates an eight second data acquisition in accordance with step 110 by activating the sense amplifiers 50 and 58, the analog-to-digital converter 60, the direct memory access 68, and the memory 80. The multiplexer 64 sequentially couples the sense channels 51 and 59 to the analog-to-digital converter 60 to permit the storing of digital samples of the electrograms sensed by the first electrode pair of the atrial channel 59 (electrodes 44 and 46) and the second electrode pair of the RV channel 51 (electrodes 38 and 40). The timer 73 times the eight second acquisition period and the electrogram digital samples for the entire eight seconds are stored in the memory portion 82 of the memory 80. As a result, when the acquisition period is completed, the memory portion 82 will contain electrogram digital samples of the electrogram signals sensed by sense channels 51 and 59 during the entire eight second acquisition period.

After completion of the eight second acquisition period, the atrial fibrillation detector 70 implements an atrial fibrillation detection algorithm by processing and applying the data stored in the memory portion 82 to an atrial fibrillation criteria to detect for atrial fibrillation in accordance with step 112. The atrial fibrillation criteria may be as described in copending application Ser. No. 08/233,251, filed Apr. 6, 1994, in the names of Harley White and Joseph Bocek, for SELECTIVE CARDIAC ACTIVITY ANALYSIS ATRIAL FIBRILLATION DETECTION SYSTEM AND METHOD AND ATRIAL DEFIBRILLATOR UTILIZING SAME, and/or copending application Ser. No. 08/278,055, filed Jul. 20, 1994, in the names of Jaeho Kim and Harley White, for SYSTEM AND METHOD FOR REDUCING FALSE POSITIVES IN ATRIAL FIBRILLATION DETECTION, which applications are assigned to the assignee of the present invention and incorporated herein by reference.

If atrial fibrillation is not detected, the activated sensing channels are deactivated until the next data acquisition is to be performed. However, if atrial fibrillation is detected in step 112, the microprocessor then in step 114 causes the last three seconds of the electrogram samples stored in the memory portion 82 to be transferred into the scratch pad memory portion 84. As a result, the electrogram samples of the electrogram signals occurring during the last three seconds of the data acquisition period and representing the heart activity during the detection of atrial fibrillation and as sensed by sense channels 51 and 59 will be retained in the scratch pad memory portion 84 of the memory 80.

After saving the first electrogram samples in the scratch pad memory portion 84, the atrial defibrillator 30, through the charge delivery control 74, causes the charge and storage capacitor circuit 75 to charge the storage capacitor in accordance with step 116. As the capacitor is being charged, the charge and delivery control 74 determines if the storage capacitor of circuit 75 has been charged to a preselected peak voltage. If it has not, the charge and delivery control will continue to cause the charge and storage capacitor circuit 75 to continue charging the storage capacitor. When the charge and delivery control 74 determines that the capacitor is charged, the defibrillator will perform another eight second acquisition period in accordance with step 118. The electrogram samples from sense channels 51 and 59 acquired during this further eight second acquisition period are stored in the memory portion 82.

After step 118, the data check stage 78 in step 120 evaluates the data stored in memory portion 82 to determine if it satisfies certain data quality criteria. The data quality criteria may relate to the presence of noise in the stored data, the data representing electrogram signals of too high or low an amplitude to be processed reliably by the atrial fibrillation detector, or the data representing a heart rate which is too high for reliable processing by the atrial fibrillation detector. If the data does not satisfy the quality criteria, it is then saved in step 122 by the memory control 79 transferring the data to the scratch pad 84. Following the transfer to the scratch pad 84, the data is then transferred in step 124 by the memory control 79 to memory portion 89 for more permanent storage and later retrieval. The default data thus stored will then be of assistance in determining why the therapy intervention was terminated without a cardioversion attempt being made.

If in step 120 it is determined that the stored data satisfies the quality criteria, the atrial fibrillation detector 70, in step 126, determines from the data stored in memory portion 82 if the atria are still in fibrillation. If the atria are not still in fibrillation, the data is saved as default data in step 128 and then in step 124 more permanently stored for future retrieval, as previously described. However, if the atria are still in fibrillation, the microprocessor 66 then moves to the next step 130 wherein it acquires another eight seconds of data. This data is acquired from sense channels 51 and 53, is stored in memory portion 82, and is analyzed in step 132 to determine if the electrogram signals which will be used to synchronize the attempted cardioversion will be satisfactory for that purpose. To that end, the check signals stage 71 evaluates the data to determine if it satisfies qualifying criteria relating to signal amplitudes, noise, or heart rate, for example. If the data does not satisfy the qualifying criteria, it is then saved in step 134 in a manner as previously described.

If the check signals stage 71 determines that the data qualifies to permit the synchronized cardioversion to proceed, it causes the timer 73 to be reset for timing a pre-set time period in step 136. The synchronization process or protocol then begins in step 138 wherein an energy application timing criteria is applied by the sync protocol stage 72 to the heart activity sensed in sense channels 51 and 53 to identify an appropriate R wave for synchronizing the cardioversion attempt. The energy application timing criteria may include the aforementioned minimum interval criteria and other criteria as described, for example, in copending application Ser. No. 08/259,476, filed Jun. 14, 1994, in the name of Harley White, for CARDIOVERSION SYNCHRONIZATION SYSTEM AND METHOD FOR AN ATRIAL DEFIBRILLATOR, which application is assigned to the assignee of the present invention and incorporated herein by reference.

In performing the synchronization protocol the process first pauses for three seconds to permit three seconds of data to be stored in memory portion 82. As a result of this pause, if an appropriate R wave on which to synchronize is immediately found, three seconds of such data will be stored in memory portion 82 at the time the cardioverting energy is delivered.

During the synchronization protocol, electrogram data from all three channels 51, 53 and 59 is stored, and the direct memory access 68 continuously addresses the memory locations of the memory portion 82 on a recirculating basis. Upon the completion of the synchronization protocol, the memory portion 82 will contain electrogram digital samples of the electrogram signals sensed by all three channels 51, 53 and 59 during at least the last three seconds of the synchronization protocol. Also during the synchronization protocol, as represented in step 140, the timer is repeatedly interrogated to determine if it has timed out. If the timer has not timed out, it is then determined if cardioversion has been attempted as denoted by step 142. If the timer times out after, for example, one minute, before a cardioversion is attempted, it is then assumed that synchronization conditions have adversely changed and that cardioversion should not therefore be attempted. If this occurs, the last three seconds of synchronization data stored in memory portion 82 is saved in steps 144 and 124 as default data, as previously described.

If an appropriate R wave is identified before timer 73 times out, the charge deliver control 74 causes the discharge circuit 77 to discharge a portion of the energy stored in the storage capacitor of circuit 75 between electrodes 44 and 46 for cardioverting the atria of the heart. During this time, data from the sense channels 51, 53 and 59 continues to be stored in memory portion 82. Since electrodes 44 and 46 are used to apply the cardioverting electrical energy, sense amplifiers 52 and 58 are preferably protected by input protective circuitry well known in the art to prevent the cardioverting energy from damaging sense amplifiers 52 and 58. Even though sense amplifier 52 is essentially blanked during this time, its output will continue to be coupled to the analog-to-digital converter 60 by multiplexer 64 because it will still provide useful data. For example, when sense amplifier 52 is blanked, the initial blanking will provide the time in which the cardioverting energy was applied. This information can be used to confirm energy delivery and the time during the patient's cardiac cycle in which the energy was delivered to verify proper synchronization. When sense amplifier 52 recovers, it will once again provide EGM data for storage.

During cardioversion, the RV channel 51 is also blanked, but for a shorter time. This allows the sense amplifier 50 to recover more quickly. Even though the channel 51 is blanked for a short time, data provided by the RV channel 51 is still stored during this time and is particularly useful to confirm that the cardioverting energy was delivered at an appropriate and safe time.

Following energy discharge, data storage, now also including data from channel 59, continues for a time period of four seconds, for example. During this time, the counter 76 in step 146 is incremented to indicate the number of cardioversion attempts which have been completed for this atrial fibrillation episode.

Upon the termination of the storing of the electrogram samples in the memory portion 82, the memory portion 82 will include electrogram samples of the electrogram signals provided by all three sense channels 51, 53 and 59 continuously over a seven second interval, beginning three seconds prior to and ending four seconds after the delivery of the cardioverting electrical energy to the atria. The data thus stored in the memory portion 82 provides the cardiologist with useful information relating to both the time at which the cardioverting electrical energy is applied to the heart relative to particular features of the heart activity such as an R wave from data from RV channel 51 and RVCS channel 53 and the return of the atria to normal sinus rhythm from data from atrial channel 59. After step 146, the microprocessor in step 148 transfers the last seven seconds of data stored in memory portion 82 into the scratch pad memory portion 84. This conditions the memory portion 82 for a further data acquisition in step 150.

In step 150, another eight second data acquisition is performed as previously described for further atrial fibrillation detection in step 156. Once again, the check data stage 78 evaluates the quality of the data in step 152 and saves the data in step 154 as default data if it fails to satisfy the data quality criteria. If the data satisfies the data quality criteria and if the atrial fibrillation has been successfully cardioverted, the memory control 79 causes the data stored in the scratch pad memory portion 84 to be transferred, in step 124, to the memory portions 86 and 88 so that the memory portion 86 will include electrogram digital samples (EGM1) for electrogram signals relating to the initial detection of the atrial fibrillation episode of the heart, and memory portion 88 will include digital samples (EGM2) of electrogram signals which relate to the successful cardioversion of the atrial fibrillator.

If in step 156 it is determined that the heart is still in atrial fibrillation, the microprocessor then proceeds to step 158 to determine if the number of applications of cardioverting electrical energy delivered to the heart to cardiovert the present atrial fibrillation episode equals a preselected number of applications (N). If in step 158 the microprocessor 66 determines that the counter has not reached the predetermined number of counts (N), the microprocessor returns to step 116 to repeat the cardioversion process.

If the count (N) has been reached, the microprocessor then performs step 124, as previously described. At this point, a predetermined number of applications of electrical cardioverting energy have been applied to the heart without successfully cardioverting the atria. At this time, the memory portion 86 will include electrogram digital samples (EGM1) relating to the initial detection of the atrial fibrillation episode, and the memory portion 88 will include electrogram digital samples (EGM2) relating to the last cardioverting attempt.

As a result of the foregoing, if the atrial defibrillator should, for some reason, fail to complete its intervention for an atrial fibrillation episode, data is stored in memory 80, representing electrogram digital samples relating to the initial detection of the atrial fibrillation (EGM1), and electrogram digital samples relating to failure of the data to satisfy a predetermined criteria required for cardioversion. Upon retrieval of this data, the cardiologist will have useful information for making necessary parameter changes or deciding upon other corrective actions.

While a particular embodiment of the present invention has been shown and described, modifications may be made, and it is therefore intended in the appended claims to cover all such changes and modifications which fall within the true spirit and scope of the invention.

What is claimed is:

1. A defibrillator for defibrillating a heart in a mammalian body comprising:

sensing means for sensing electrical activity of a heart and generating heart activity data;

processing means for analyzing said heart activity data to determine if said data satisfies a predetermined criteria;

cardioverting means responsive to said processing means for applying cardioverting electrical energy to the heart when said data satisfies said predetermined criteria; and memory in communication with said processing means including one or more data storage locations for retaining at least a portion of said data when said data fails to satisfy said predetermined criteria, said retained data being accessible from the exterior of said mammalian body.

2. A defibrillator as defined in claim 1 wherein said processing means includes a fibrillation detector, wherein said predetermined criteria includes fibrillation criteria, and wherein said fibrillation detector determines if said data satisfies said fibrillation criteria.

3. A defibrillator as defined in claim 2 wherein said predetermined criteria further includes data quality criteria and wherein said processing means further includes data quality evaluating means for determining if said data satisfies said data quality criteria prior to said fibrillation detector determining if said data satisfies said fibrillation criteria.

4. A defibrillator as defined in claim 2 wherein said predetermined criteria further includes energy application timing criteria and wherein said processing means further includes energy application control means for determining if said data satisfies said energy application timing criteria for causing said cardioverting means to apply said cardioverting energy to the heart in timed relation to the heart activity.

5. A defibrillator as defined in claim 4 wherein said predetermined criteria further includes data qualifying criteria, and wherein said processing means further includes data evaluating means for determining if said data satisfies said data qualifying criteria to permit said energy application control means to determine if said data satisfies said energy application timing criteria.

6. A defibrillator as defined in claim 4 further including a timer and wherein the memory is responsive to said timer for retaining said at least a portion of said data in the one or more data storage locations when said data fails to satisfy said energy application timing criteria within a pre-set time period.

7. A defibrillator as defined in claim 1 wherein said sensing means generates first heart activity data, wherein said processing means analyzes said first heart activity data to determine if said first heart activity data satisfies said predetermined criteria, wherein said sensing means generates second heart activity data only if said first heart activity data satisfies said predetermined criteria, wherein said processing means analyzes said second heart activity data to determine if said second heart activity data also satisfies said predetermined criteria, wherein said cardioverting means applies cardioverting electrical energy to the heart if said second heart activity data also satisfies said predetermined criteria, and wherein the memory stores at least a portion of said second heart activity data if said second heart activity data fails to satisfy said predetermined criteria.

8. An atrial defibrillator for applying cardioverting electrical energy to the atria of a heart in a mammalian body when the atria are in need of cardioversion, said atrial defibrillator comprising:

sensing means for sensing atrial activity of the heart and generating atrial activity data;

a memory for storing atrial activity data generated by said sensing means;

processing means including an atrial fibrillation detector for determining if said atrial activity data satisfies atrial fibrillation criteria;

cardioverting means for applying cardioverting electrical energy to the atria if said atrial activity data satisfies said atrial fibrillation criteria;

the memory being in communication with said processing means and including one or more data storage locations; and, storage control means for causing at least a portion of said atrial activity data to be retained in the one or more data storage locations of the memory when said atrial activity data fails to satisfy said atrial fibrillation criteria, said retained data being accessible from the exterior of the mammalian body.

9. An atrial defibrillator as defined in claim 8 wherein said processing means further includes data quality evaluating means for determining if said atrial activity data satisfies data quality criteria, said atrial fibrillation detector determining if said atrial activity data satisfies said atrial fibrillation criteria if said atrial activity data satisfies said data quality criteria, and said storage control means causing said at least a portion of said atrial activity data to be retained in the one or more data storage locations of the memory when said atrial activity data fails to satisfy said data quality criteria.

10. An atrial defibrillator as defined in claim 8 further including second sensing means for sensing ventricular activity of the heart and generating ventricular activity data, wherein said processing means further includes energy application control means for determining if said ventricular activity data satisfies energy application timing criteria for causing said cardioverting means to apply said cardioverting energy to the heart in timed relation to the ventricular activity.

11. An atrial defibrillator as defined in claim 10 further including a timer and wherein said storage control means is responsive to said timer for causing at least a portion of said ventricular activity data to be retained in the one or more data storage locations of the memory when said ventricular activity data fails to satisfy said energy application timing criteria within a pre-set time period.

12. An atrial defibrillator as defined in claim 10 wherein said processing means further includes data evaluating means for determining if said ventricular activity data satisfies ventricular activity data qualifying criteria to permit said energy application control means to determine if said data satisfies said energy application timing criteria, and said storage control means causing said memory means to retain at least a portion of said ventricular activity data in the one or more data storage locations when said ventricular activity data fails to satisfy said ventricular activity data qualifying criteria.

13. An atrial defibrillator as defined in claim 8 wherein said sensing means generates first atrial activity data, wherein said processing means analyzes said first atrial activity data to determine if said first atrial activity data satisfies said atrial fibrillation criteria, wherein said sensing means generates second atrial activity data only if said first atrial activity data satisfies said predetermined criteria, wherein said processing means analyzes said second atrial activity data to determine if said second atrial activity data also satisfies said atrial fibrillation criteria, wherein said cardioverting means applies cardioverting electrical energy to the heart if said second atrial activity data also satisfies said predetermined criteria, and wherein the memory retains at least a portion of said second atrial activity data in the one or more data storage locations when said second atrial activity data fails to satisfy said atrial fibrillation criteria.

14. An atrial defibrillator as defined in claim 8 wherein said defibrillator is an implantable defibrillator and wherein said defibrillator further includes transmitting means for transmitting the retained data to a nonimplanted, external receiver.

15. A method of defibrillating a heart in a mammalian body, said method including the steps of:

sensing electrical activity of the heart and generating heart activity data;

analyzing said heart activity data to determine if said data satisfies a predetermined criteria;

applying cardioverting electrical energy to the heart when said data satisfies said predetermined criteria; and retaining at least a portion of said data in a memory accessible from the exterior of the mammalian body when said data fails to satisfy said predetermined criteria.

16. A method as defined in claim 15 wherein said predetermined criteria includes fibrillation criteria.

17. A method as defined in claim 16 wherein said predetermined criteria further includes data quality criteria and wherein said method further includes the step of determining if said data satisfies said data quality criteria prior to determining if said data satisfies said fibrillation criteria.

18. A method as defined in claim 16 wherein said predetermined criteria further includes energy application timing criteria and wherein said method further includes the step of determining if said data satisfies said energy application timing criteria, said energy application timing criteria causing said cardioverting means to apply said cardioverting energy to the heart in timed relation to the heart activity.

19. A method as defined in claim 18 wherein said predetermined criteria further includes data qualifying criteria, and wherein said method further includes the step of determining if said data satisfies said data qualifying criteria prior to determining if said data satisfies said energy application timing criteria.

20. A method as defined in claim 18 further including the step of retaining said at least a portion of said data if said data fails to satisfy said energy application timing criteria within a pre-set time period.

\* \* \* \* \*

UNITED STATES PATENT AND TRADEMARK OFFICE
CERTIFICATE OF CORRECTION

PATENT NO. : 5,507,780
DATED : April 16, 1996
INVENTOR(S) : David P. Finch

It is certified that error appears in the above-identified patent and that said Letters Patent is hereby corrected as shown below:

| Column | Line | |
|---|---|---|
| 1 | 18 | "redirect" should be --redetect-- |
| 3 | 56 | DELETE "-" between --sensing means-- |

Signed and Sealed this

Twenty-third Day of July, 1996

Attest:

BRUCE LEHMAN

Attesting Officer     Commissioner of Patents and Trademarks